United States Patent
Kanai et al.

(10) Patent No.: US 9,194,849 B2
(45) Date of Patent: Nov. 24, 2015

(54) COLUMN UNIT AND GAS CHROMATOGRAPHY DEVICE PROVIDED WITH THE SAME

(71) Applicant: SHIMADZU CORPORATION, Kyoto-shi, Kyoto (JP)

(72) Inventors: Masaki Kanai, Nara (JP); Takahiro Nishimoto, Kyoto (JP); Masanori Nishino, Joyo (JP); Satoshi Matsuoka, Tokyo (JP)

(73) Assignee: SHIMADZU CORPORATION, Kyoto (JP)

( * ) Notice: Subject to any disclaimer, the term of this patent is extended or adjusted under 35 U.S.C. 154(b) by 43 days.

(21) Appl. No.: 14/226,018

(22) Filed: Mar. 26, 2014

(65) Prior Publication Data
US 2014/0290491 A1 Oct. 2, 2014

(30) Foreign Application Priority Data
Apr. 2, 2013 (JP) .................. 2013-076573

(51) Int. Cl.
| | | |
|---|---|---|
| G01N 30/30 | (2006.01) | |
| G01N 30/60 | (2006.01) | |
| G01N 30/02 | (2006.01) | |

(52) U.S. Cl.
CPC ............ G01N 30/30 (2013.01); G01N 30/6052 (2013.01); G01N 30/6095 (2013.01); *G01N 2030/025* (2013.01); *G01N 2030/303* (2013.01);
(Continued)

(58) Field of Classification Search
CPC .............. G01N 30/30; G01N 30/6091; G01N 30/6095; G01N 2030/3007; G01N 2030/303; G01N 2030/3053; G01N 2030/3061; G01N 2030/3084; G01N 2030/6056; G01N 30/6052
See application file for complete search history.

(56) References Cited

U.S. PATENT DOCUMENTS

| | | | | |
|---|---|---|---|---|
| 5,005,399 A | * | 4/1991 | Holtzclaw et al. ............ 73/23.39 |
| 5,094,815 A | * | 3/1992 | Conboy et al. .................. 422/52 |
| 5,298,225 A | | 3/1994 | Higdon | |

(Continued)

FOREIGN PATENT DOCUMENTS

| | | |
|---|---|---|
| CN | 201886009 U | 6/2011 |
| JP | 05-087793 A | 4/1993 |
| JP | 11-023553 A | 1/1999 |

OTHER PUBLICATIONS

Wang et al., "Gas chromatography using resistive heating technology", Journal of Chromatography A, vol. 1261, 2012, p. 1-12 (46-57).

(Continued)

*Primary Examiner* — Robert Clemente
(74) *Attorney, Agent, or Firm* — Westerman, Hattori, Daniels & Adrian, LLP (57) ABSTRACT

A housing of a column unit is tubular-shaped, and includes a first opening and a second opening, and an inner space separated from outside air by an insulating material. An air cooling section including a cooling device is arranged on a side of the first opening of the housing. At the time of cooling the inside of the inner space of the housing, air is caused, by a fan, to flow through the air cooling section and from the side of the first opening to a side of the second opening. A column section including a separation column and a heater is arranged inside the housing. A gap through which air flows from the first opening to the second opening is formed between the column section and an inner wall of the inner space of the housing.

10 Claims, 6 Drawing Sheets

(52) U.S. Cl.
CPC  *G01N 2030/3007* (2013.01); *G01N 2030/3061* (2013.01); *G01N 2030/3084* (2013.01)

(56) References Cited

U.S. PATENT DOCUMENTS

| | | | |
|---|---|---|---|
| 5,808,178 A * | 9/1998 | Rounbehler et al. | 73/23.39 |
| 6,530,260 B1 | 3/2003 | Mustacich et al. | |
| 6,682,699 B2 | 1/2004 | Mustacich et al. | |
| 7,524,363 B2 * | 4/2009 | Bentley et al. | 96/101 |

OTHER PUBLICATIONS

Office Action dated May 19, 2015, issued in counterpart Chinese Patent Application No. 201410122702.7 w/English translation of its Search Report (9 pages).

* cited by examiner

COLUMN UNIT AND GAS CHROMATOGRAPHY DEVICE PROVIDED WITH THE SAME

BACKGROUND OF THE INVENTION

1. Field of the Invention

The present invention relates to a column unit for performing temperature control of a separation column, and a gas chromatography device provided with the column unit.

2. Description of the Related Art

Many of the gas chromatography devices that are currently on the market accommodate a separation column in a forced convection oven that reduces the temperature distribution inside the oven by causing the air inside to convect by force, and to perform temperature control of the separation column. Heating of the separation column by such a forced convection oven has advantages that thermal uniformity inside the oven may be easily achieved, and also, that the influence of the ambient temperature is not easily received.

On the other hand, since the oven itself has a high heat capacity, there is a disadvantage that it is difficult to increase the rate of temperature increase and the rate of temperature decrease of the column. The rate of temperature increase affects the time required until the temperature inside the oven becomes stable, and if the rate of temperature increase is low, the time required until an analysis is started becomes long, thereby increasing the time required for the analysis. Also, in the case of performing a temperature increase analysis of performing an analysis while raising the temperature of the separation column at a constant rate, if the rate of temperature increase is low, the time required for one temperature increase analysis becomes long. Therefore, to reduce the time required until the start of an analysis or the time required for an analysis, the rate of temperature increase of the separation column has to be increased. However, the rate of temperature increase of a gas chromatography device that uses a forced convection oven, which is currently in practical use, is 60° C./min or less.

In recent years, gas chromatography devices provided with a heat-transfer temperature control unit for performing temperature control of a separation column by heat transfer from a heater without involving air are being proposed and applied (see U.S. Pat. Nos. 6,682,699, 6,530,260, and 5,298,225). The heat capacity of such a heat-transfer temperature control unit is smaller than that of a convection oven, and a temperature increase analysis may therefore be performed at an increased rate, but since the heat capacity thereof is small, the influence of the ambient temperature is easily perceptible. Accordingly, a heat insulation treatment is performed on the temperature control unit including a separation column by covering the unit with an insulating material or by enclosing the unit with a housing so that influence of the ambient temperature is not easily received.

According to the gas chromatography device, the separation column may have to be cooled to or below the temperature of the room, it is in depending on an analysis sample. In the case of cooling the separation column to or below the room temperature in the forced convection oven, the oven itself has to be cooled to or below the room temperature by introducing cooled carbon dioxide or nitrogen gas, and the cooling mechanism will be large and complicated, and also, as with heating, it is difficult to performing cooling at a high rate.

With the gas chromatography device provided with a heat-transfer temperature control unit, if a heat insulation treatment is performed around the separation column to reduce the influence of the ambient temperature on the separation column, the rate of temperature increase may be increased, but the efficiency of heat dissipation to surroundings is reduced, and the rate of cooling is reduced. In the case of repeatedly performing the temperature increase analysis, when a temperature increase analysis is performed, the separation column has to be cooled to a predetermined temperature to perform the next temperature increase analysis, and the total time necessary for one temperature increase analysis is the sum of the temperature increase analysis time and the cooling time. Accordingly, to increase the operating rate at the time of repeatedly performing the temperature increase analysis, it is important that the cooling time is reduced together with the temperature increase time.

Cooling of a separation column by providing a heat-transfer temperature control unit with a Peltier device is proposed (see "Gas chromatography using resistive heating technology", A. Wang et. al, Journal of Chromatography, Vol. 1261, pp. 46-57, 2012). By providing a Peltier device to the temperature control unit, the cooling efficiency for the separation column may be increased while enhancing the heat insulation of the separation column. However, since generally, a Peltier device cannot be used at a high temperature of 200° C. or higher, it is difficult to use the temperature control unit provided with a Peltier device for the purpose of analyzing for example a high-boiling component.

SUMMARY OF THE INVENTION

An object of the present invention is to provide a column unit whose rates of temperature increase and temperature decrease are high, and which may be used under a high temperature condition, and a gas chromatography device provided with the column unit.

A column unit according to the present invention includes a tubular housing including a first opening (air inlet) and a second opening (air outlet), and an inner space separated from outside air by an insulating material. An air cooling section including a cooling device is arranged on a side of the first opening of the housing. A fan is arranged on a side of the first or second opening of the housing, the fan being controlled to operate, when cooling an inside of the inner space, to cause air to flow through the air cooling section in a direction from the side of the first opening to a side of the second opening, and not to operate when heating the inside of the inner space or maintaining the inside of the inner space at a constant temperature.

Furthermore, a column section including a separation column, and a heater for heating the separation column is arranged in the inner space of the housing. A gap through which air flows from the first opening to the second opening when the fan is operated is formed between the column section and an inner wall of the inner space.

According to the column unit of the present invention, the column section is arranged on the air flowing path inside the housing, and the air cooled by the cooling device of the air cooling section is supplied to the inner space, and thus, the column section may be efficiently cooled by the cooled air at the time of cooling of the separation column, and the rate of cooling may be increased. Since the inner space of the housing is separated from the outside air by the insulating material, the column section is not easily affected by the change in the temperature outside the housing, and the separation column may be highly efficiently heated by the heater at the time of temperature increase of the separation column by the insulating effect of the insulating material. The cooling device of the air cooling section is arranged on the upstream side, in the flow direction of air, of the first opening, that is, outside the air inlet of the housing, and is thermally separated from the heater of the column section, and the cooling device is not directly exposed to the heat from the heater of the column section, and the separation column may be used under a high temperature condition, such as 200° C. or higher.

The gas chromatography device according to the present invention includes the column unit of the present invention, a sample injection section connected to an end of a separation column of the column unit, and a detector connected to another end of the separation column.

According to the gas chromatography device of the present invention, since the column unit of the present invention whose rates of temperature increase and temperature decrease are high is used, the time required until the separation column temperature becomes stable at the start of an analysis, and the time required for one temperature increase analysis become short compared to a conventional gas chromatography device.

DETAILED DESCRIPTION OF THE PREFERRED EMBODIMENTS

A column unit of the present invention preferably further includes a temperature sensor for measuring the temperature of a separation column or the ambient temperature of the separation column, and a temperature control section for controlling the operations of a heater and an air cooling section based on measured temperature of the temperature sensor. The temperature of the separation column may then be controlled accurately.

An air inlet door for opening or closing an air inlet of a housing is preferably provided between a cooling device and an air inlet, and the temperature control section preferably controls the operation of the air inlet door in such a way that the air inlet door closes at the time of heating of the separation column, and opens at the time of cooling of the separation column. By the air inlet of the housing closing at the time of raising the temperature of the separation column, the heating efficiency of the inner space is increased and the rate of temperature increase of the separation column may be further increased. Also, since the heated air inside the inner space is prevented from flowing to the cooling device side, the cooling device is not easily affected by the heat at the time of raising the temperature of the separation column to a high temperature.

An air outlet door for opening or closing an air outlet is preferably further provided, and the temperature control section preferably also controls the operation of the air outlet door in such a way that, in addition to the air inlet door, the air outlet door also closes at the time of heating of the separation column, and opens at the time of cooling of the separation column. Then, the heating efficiency of the inner space at the time of raising the temperature of the separation column is increased, and the rate of temperature increase of the separation column may be further increased.

To control the operation of the air cooling section by the temperature control section, the number of revolutions of a fan of the air cooling section may be controlled.

Also, the separation column is preferably formed in a flat shape. As a heater for this case, a flat heater that is in contact with one side of the separation column may be cited.

Figure 1:
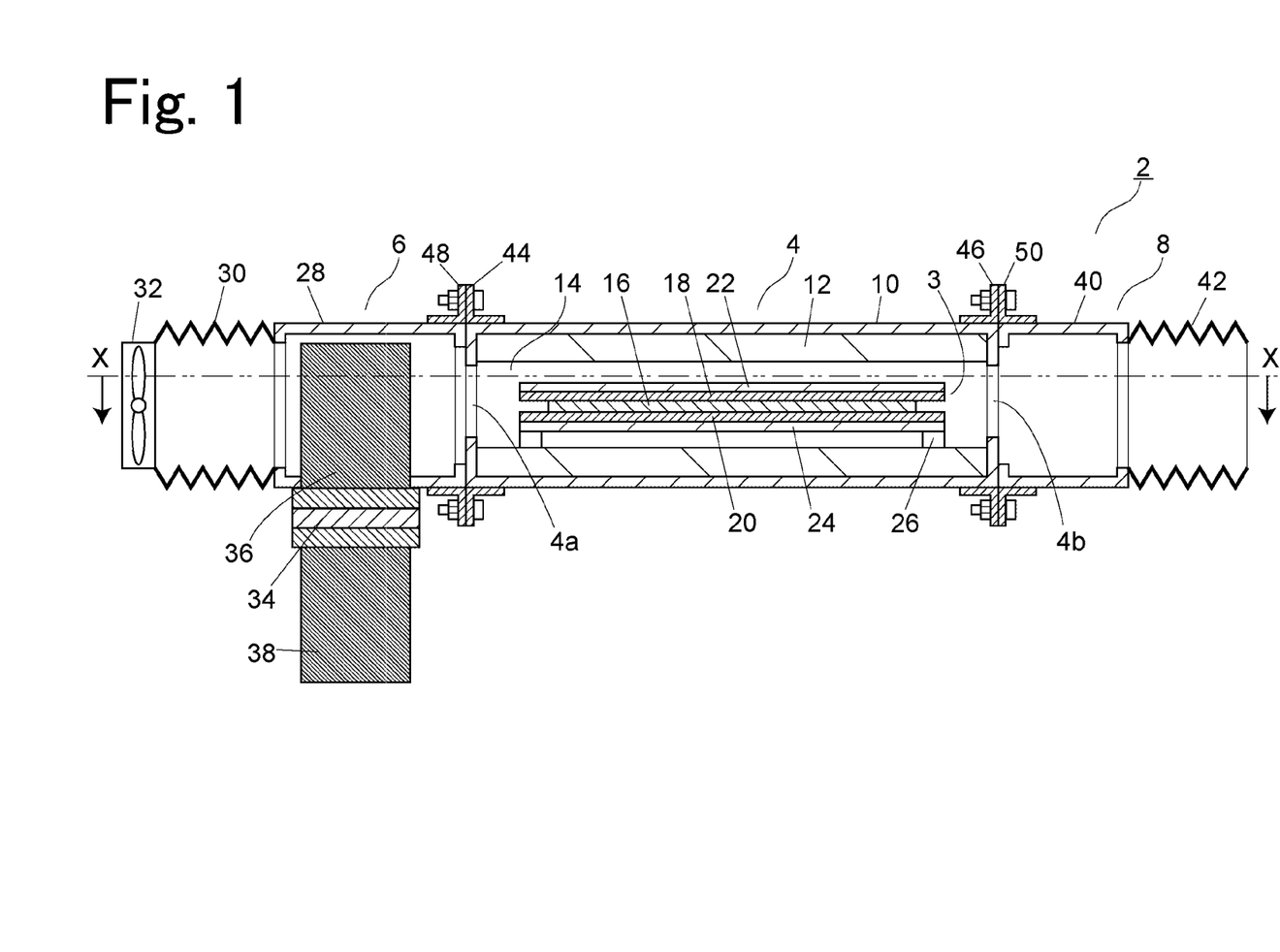
FIG. 1 is a cross-sectional diagram showing an example of a column unit.
Figure 2:
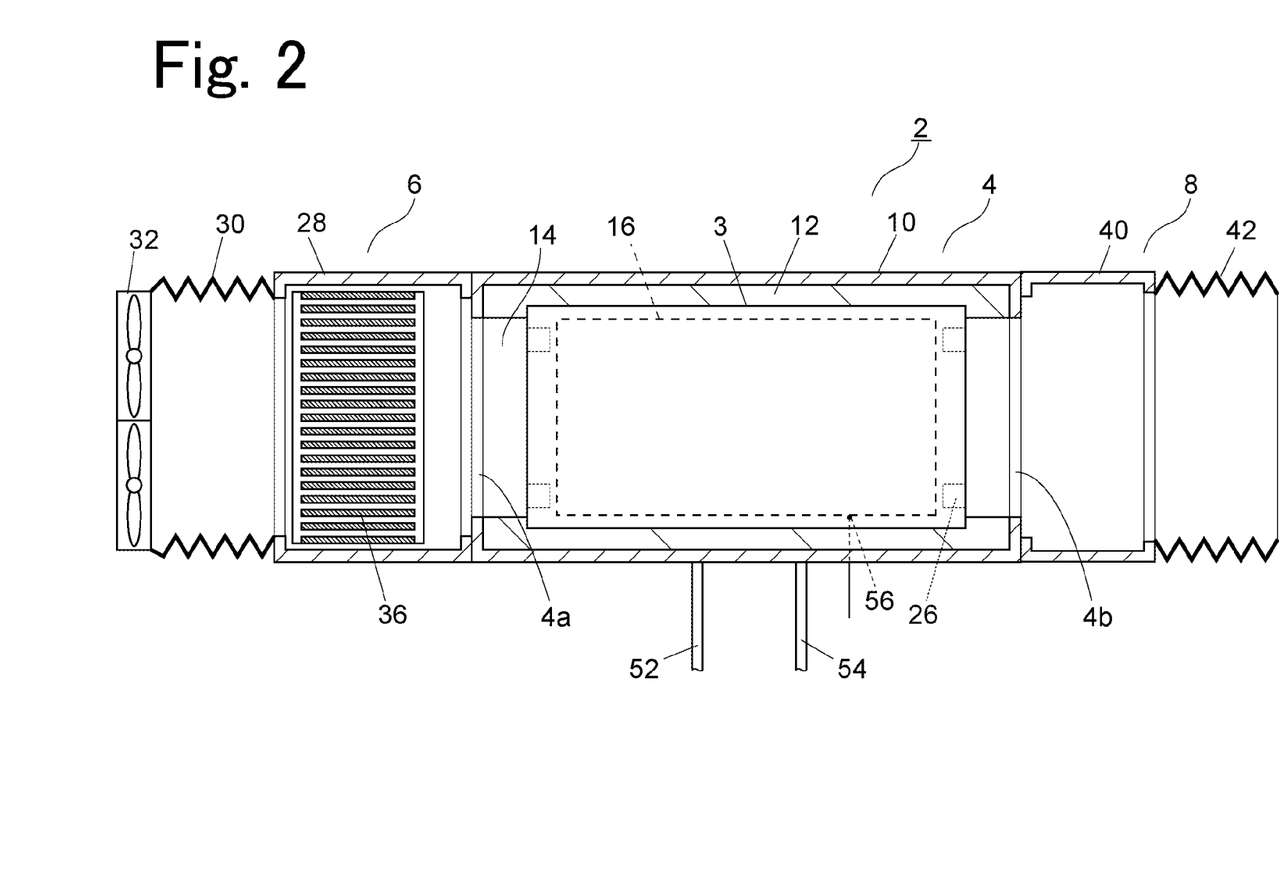
FIG. 2 is a cross-sectional diagram at X-X position of FIG. 1.
Figure 3:
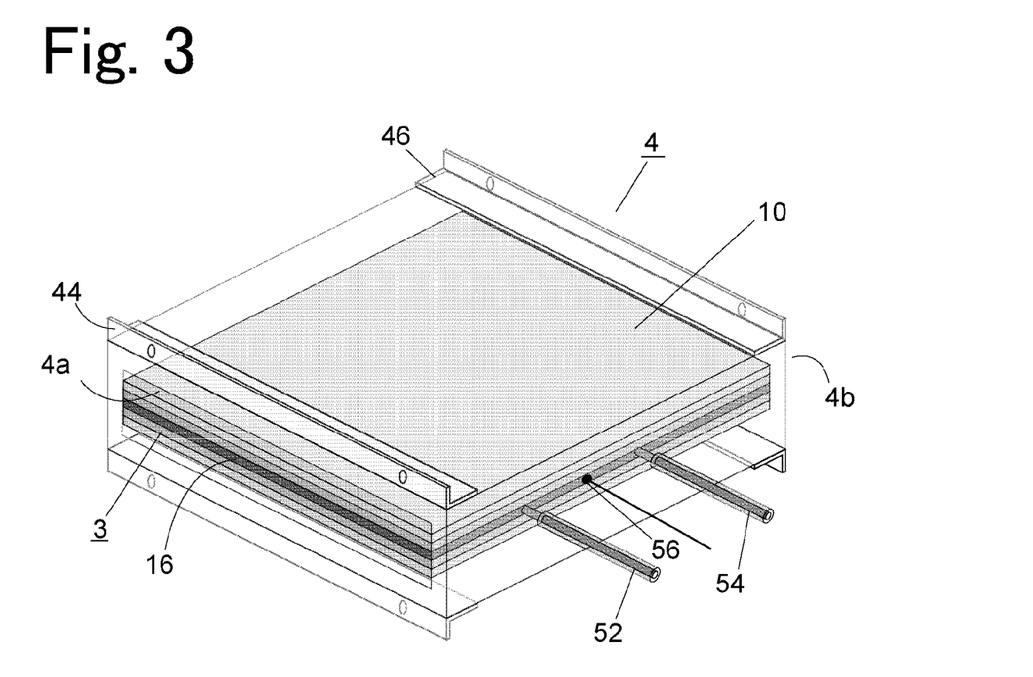
FIG. 3 is a perspective view showing a housing portion of the present example.

The structure of an example of the column unit will be described with reference to FIGS. 1 to 3. FIG. 1 is a cross-sectional diagram showing an example of the column unit, FIG. 2 is a cross-sectional diagram at X-X position of FIG. 1, and FIG. 3 is a perspective view showing a housing portion of the example. It is to be noted that in FIG. 3, a housing 10 and an insulating material 12 are shown in a transparent manner so that the inner structure may be seen.

A column unit 2 is configured by a column cartridge 4, an air cooling section 6, and an air outlet section 8. The column cartridge 4 has a space 14 within, and is provided with an air inlet 4a at one side surface to take cooling air into the space 14, and an air outlet 4b at the other side surface. The air cooling section 6 is attached to the side surface of the column cartridge 4 where the air inlet 4a is provided, and the air outlet section 8 is attached to the side surface where the air outlet 4b is provided. The column cartridge 4 and the air cooling section 6 are joined together by having respective mounting brackets 44 and 48 fixed by a bolt and a nut, and the column cartridge 4 and the air outlet section 8 are joined together by having respective mounting brackets 46 and 50 fixed by a bolt and a nut.

The column cartridge 4 is configured by the stainless steel housing 10 having, for example, a square tube shape, the housing 10 enclosing the outer periphery of the column cartridge 4, and the insulating material 12 covering most of the inner wall surface of the housing 10. The inner space 14 is thereby separated from the outside air by the insulating material 12. A column section 3 is arranged inside the inner space 14. The column section 3 has a flat shape. The column section 3 is configured in such a way that a separation column 16 is sandwiched between two flat heaters 18 and 20, the separation column 16 including a flat channel substrate having an inner channel as a separation channel, and metal plates 22 and 24, as back plates, are attached to the outer surfaces of the heaters 18 and 20, respectively. The back plates 22 and 24 are for example stainless steel plates. The back plates 22 and 24 are provided to increase the thermal contact between the flat heaters 18 and 20, and the separation column 16 by the flat heaters 18 and 20 being pressed against the separation column 16. The back plates 22 and 24 are joined together by screws or the like. The heaters 18 and 20 are for example stainless steel heaters or mica heaters.

The separation column 16 is formed by forming a groove whose width is 100 µm and whose depth is 100 µm to a silicon substrate, for example, by using MEMS (Micro Electro Mechanical Systems), and anodically bonding PYREX (registered trademark) glass on the surface of the silicon substrate where the groove is formed. The groove formed to the silicon substrate becomes the inner channel by bonding a glass substrate to the silicon substrate, and the inner channel is made the separation channel, and thus, the inner wall of the channel is coated with polydimethylsiloxane as a liquid phase.

The structure of the column section 3 is not restricted to the above, and a structure according to which the flat heater is in contact with a capillary column, or a structure according to which a heating wire is wound around a capillary column is also possible.

Both ends of the inner channel of the separation column 16 are drawn to the outside of the column cartridge 4 by transfer tubes 52 and 54. The transfer tube 52 is a pipe for connecting one end of the inner channel of the separation column 16 to a sample injection section, and the transfer tube 54 is a pipe for connecting the other end of the inner channel of the separation column 16 to a detector. In the perspective view shown in FIG. 3, the transfer tubes 52 and 54 extend in a direction parallel to the main plane of the separation column 16, and are drawn to the outside of the column cartridge 4 from a side face of the column cartridge 4, but the direction of drawing out of both ends of the inner channel of the separation column 16 is not restricted thereto. According to an example of a gas chromatography device of FIG. 7 described below, both ends of the inner channel of the separation column 16 are drawn out in a direction vertical to the main plane of the separation column 16.

A temperature sensor 56 is provided in contact with the separation column 16 to measure the temperature of the separation column 16. The temperature sensor may alternatively be provided at a position for measuring the ambient temperature of the separation column 16. The ambient temperature of the separation column 16 is the temperature that is measured by the temperature sensor that is in indirect contact with the separation column 16 through a metal plate or the like, or the temperature that is measured by the temperature sensor that is separated from the separation column 16 by a small distance of for example 1 mm or less.

The column section 3 is held inside the column cartridge 4 by support members 26 at four parts on the back plate 24 side. A gap is provided between the surface, of the column section 3, on the side of the back plate 22 and the insulating material 12, and between the surface on the side of the back plate 24 and the insulating material 12, and air taken in from the air inlet 4a is caused to flow along the main planes of the column section 3. The main planes of the column section 3 refer to the top and bottom planes of the flat column 3 having large areas.

In this example, gaps are provided between the insulating material 12 and both main planes of the column section 3, but one of the main planes may be in contact with the insulating material 12. However, the cooling efficiency of the separation column 16 by the air from the air cooling section 6 is more increased if gaps are provided between the insulating material 12 and both main planes of the column section 3.

The air cooling section 6 includes a cooling tube 28, an air inlet duct 30, a cooling fan 32, a Peltier device 34 (cooling device), a cooling fin 36, and a heat dissipation fin 38. The cooling tube 28 has a square tube shape. The mounting bracket 48 for joining the cooling tube 28 to the column cartridge 4 is provided to the cooling tube 28, and one open end of the cooling tube 28 is joined to the air inlet 4a side of the column cartridge 4. One open end of the air inlet duct 30 is attached to the other open end of the cooling tube 28, and the cooling fan 32 for taking in air is attached to the other open end of the air inlet duct 30.

The cooling fin 36 is arranged inside the cooling tube 28. The cooling fin 36 is configured in such a way that a plurality of metal plates are arranged along the flow direction of the air that is taken in by the cooling fan 32, and gaps are provided between the metal plates. The air that is taken in by the cooling fan 32 is cooled while passing through the gaps of the metal plates.

The Peltier device 34 is arranged outside the cooling tube 28, and its cooling surface is in contact with the cooling fin 36. The heat dissipation surface of the Peltier device 34 is provided with the heat dissipation fin 38 having the same structure as the cooling fin 36. The Peltier device 34 conducts heat away from the cooling fin 36, and dissipates, via the heat dissipation fin 38, the heat which has been conducted away. The air cooling section 6 may, by the structure described above, cool the air taken in by the cooling fan 32 by the cooling fin 36, and supply the air into the inner space 14 of the column cartridge 4. The temperature of the separation column 16 may thereby be swiftly cooled to or below the room temperature.

The cooling fan 32 does not necessarily have to be provided on the side of the air inlet 4a of the column cartridge 4, and it may alternatively be provided on the side of the air outlet 4b. In short, it is enough if the cooling fan 32 is arranged in such a way as to cause the air to flow from the air inlet 4a of the column cartridge 4 to the air outlet 4b.

The air outlet section 8 is provided with a joining tube 40 having a Square-tube shape, and an air outlet duct 42. The joining tube 40 is provided with the mounting bracket 50 for joining the joining tube to the column cartridge 4, and one open end of the joining tube 40 is joined to the air outlet 4b side of the column cartridge 4, and the other open end of the joining tube 40 is joined to the air outlet duct 42. The air taken in by the cooling fan 32 flows through the inner space of the column cartridge 4 and is exhausted from the air outlet duct 42.

Since the air cooling section 6 is joined to the column cartridge 4 on the side of the air inlet 4a, and the air outlet section 8 is joined to the side of the air outlet 4b, the outside air is prevented from flowing into the inner space 14 from the air inlet 4a and the air outlet 4b while the cooling fan 32 is stopped and the heat insulation property of the inner space 14 is increased, compared to a case where the air cooling section 6 and the air outlet section 8 are not provided and both ends of the column cartridge 4 are directly opened to the outside. Accordingly, the rate of temperature increase at the time of raising the temperature of the separation column 16 by the heaters 18 and 20 is increased. It is to be noted that the air outlet section 8 should not necessarily be provided. The effect of preventing the outside air from flowing into the inner space 14 may also be achieved in the case where only the air cooling section 6 is provided.

The present example illustrates the column unit 2 that is horizontally arranged. In the case where the column unit 2 is in the horizontal direction, when the cooling fan 32 is not operated, the flow of air flowing into the inner space 14 is not caused, and locational temperature uniformity at the column section 3 is superior.

Figure 4:
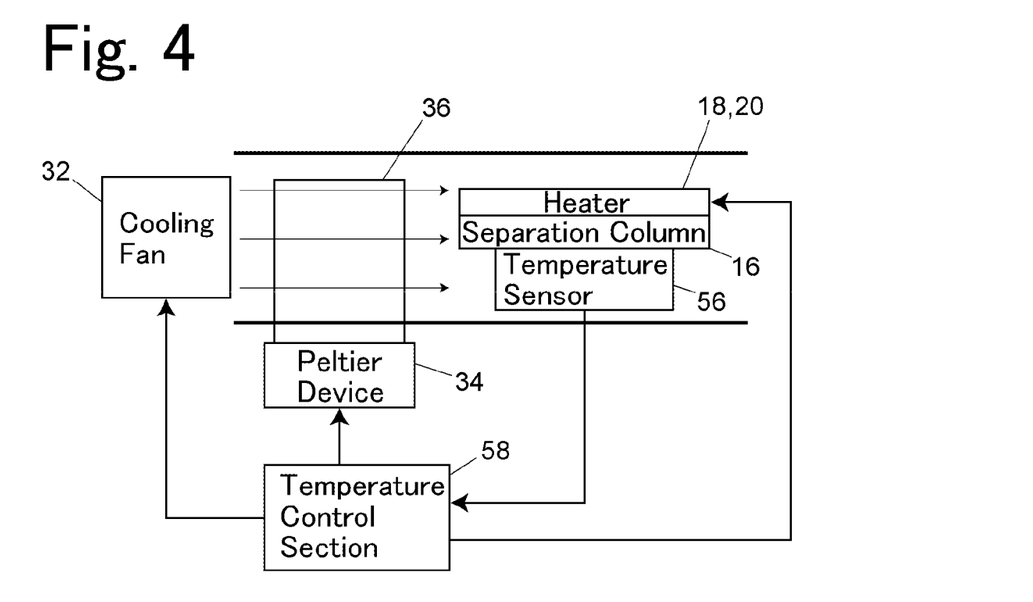
FIG. 4 is a block diagram schematically showing a control system of the present example.

FIG. 4 is a block diagram schematically showing a control system of the column unit 2.

The operations of the heaters 18 and 20, the cooling fan 32, and the Peltier device 34 are controlled by the temperature control section 58. The temperature measured by the temperature sensor 56 is loaded into the temperature control section 58. The temperature control section 58 performs control regarding on/off of the heaters 18 and 20, the cooling fan 32, and the Peltier device 34 according to analysis programs set by an analyst. The temperature sensor 56 is realized by a thermocouple attached to the back plate 22 or 24, for example. The temperature control section 58 is realized by a personal computer or a dedicated computer.

As the analysis program to be set in the temperature control section 58, a constant temperature analysis program for performing an analysis while maintaining the separation column 16 at a set temperature may be cited, and a temperature increase analysis program for performing an analysis while cooling the separation column 16 to or below the room temperature and then raising the temperature to a predetermined temperature.

In the case where the constant temperature analysis program is set, the temperature control section 58 performs feedback control of turning off the cooling fan 32 and Peltier device 34, and switching on/off of the heaters 18 and 20 in such a way that the temperature measured by the temperature sensor 56 will be at a temperature set in advance. On the other hand, in the case where the temperature increase analysis program is set, the temperature control section 58 performs control so as to cool the separation column 16 by turning on the cooling fan 32 and the Peltier 34 while maintaining the heaters 18 and 20 in an off state, and then, to raise the temperature of the separation column 16 by turning off the cooling fan 32 and the Peltier 34 and turning on the heaters 18 and 20.

The temperature control section 58 preferably also controls the number of revolutions of the cooling fan 32, in addition to on/off of the cooling fan 32. If the speed of air taken in by the cooling fan 32 is too fast and exceeds the capacity of the cooling fin 36, the air taken in by the cooling fan 32 cannot be sufficiently cooled. Accordingly, it is desirable that the number of revolutions of the cooling fan 32 is controlled and cooling wind is sent in at an appropriate speed according to the capacity of the cooling fin 36. Furthermore, depending on the type of the liquid phase of the separation column 16, the liquid phase may be damaged by drastic cooling in the cooling of the separation column 16 after the analysis. Thus, the number of revolutions of the cooling fan 32 is adjusted according to the type of the liquid phase of the separation column 16, and cooling of the separation column 16 at an appropriate cooling speed is enabled.

Figure 5:
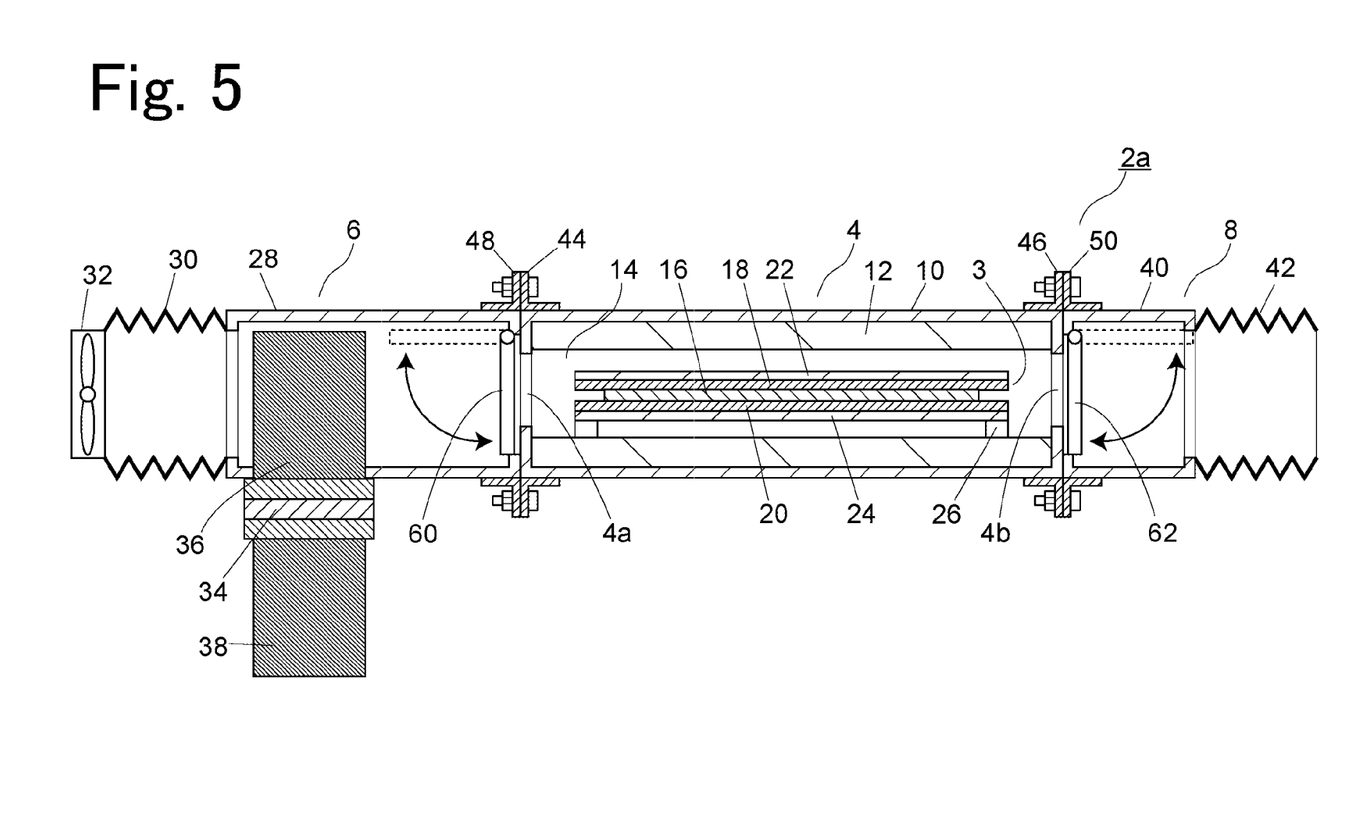
FIG. 5 is a cross-sectional diagram showing another example of the column unit.

Another example of the column unit will be described with reference to FIG. 5.

A column unit 2a of this example is different from the column unit 2 described with reference to FIGS. 1 to 4 in that the column unit 2a includes a shutter 60 (air inlet door) for opening or closing the air inlet 4a of the column cartridge 4, and a shutter 62 (air outlet door) for opening or closing the air outlet 4b. The shutters 60 and 62 are closed at the time of raising the temperature of the separation column 16, and are opened at the time of cooling the separation column 16. By closing the air inlet 4a and the air outlet 4b of the column cartridge 4 at the time of raising the temperature of the separation column 16, thermal dissipation by natural convection may be suppressed, and the heating efficiency of the separation column 16 may be further increased.

Figure 6:
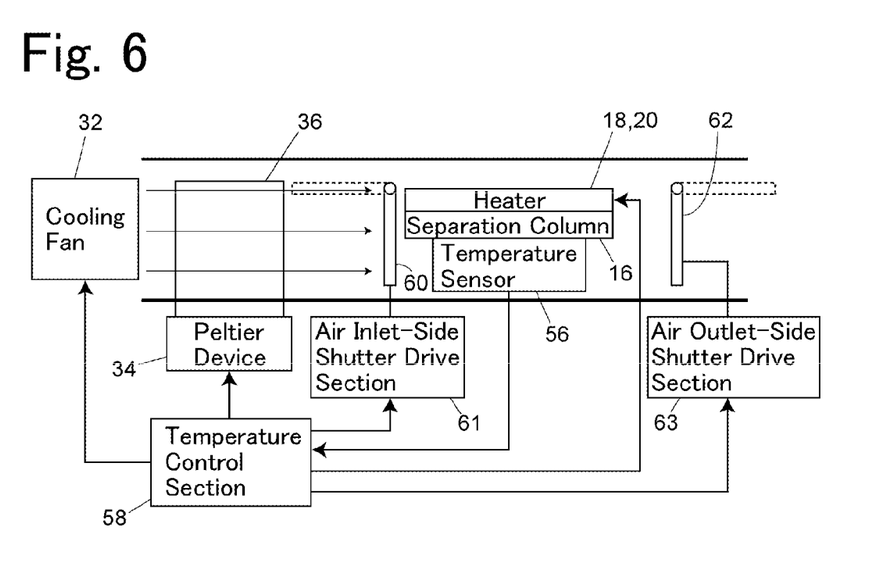
FIG. 6 is a block diagram schematically showing a control system of the present example.

As shown in FIG. 6, the operations of an air inlet-side shutter drive section 61 including a motor for driving the shutter 60, and the like, and an air outlet-side shutter drive section 63 including a motor for driving the shutter 62, and the like, are controlled by the temperature control section 58.

In the present example, the shutter 60 is provided to the cooling tube 28, and the shutter 62 is provided to the joining tube 40, but the shutters 60 and 62 may alternatively be provided inside the column cartridge 4, or at any position where opening and closing of the air inlet 4a and the air outlet 4b are enabled. Only one of the shutter 60 and the shutter 62 may be provided.

Figure 7:
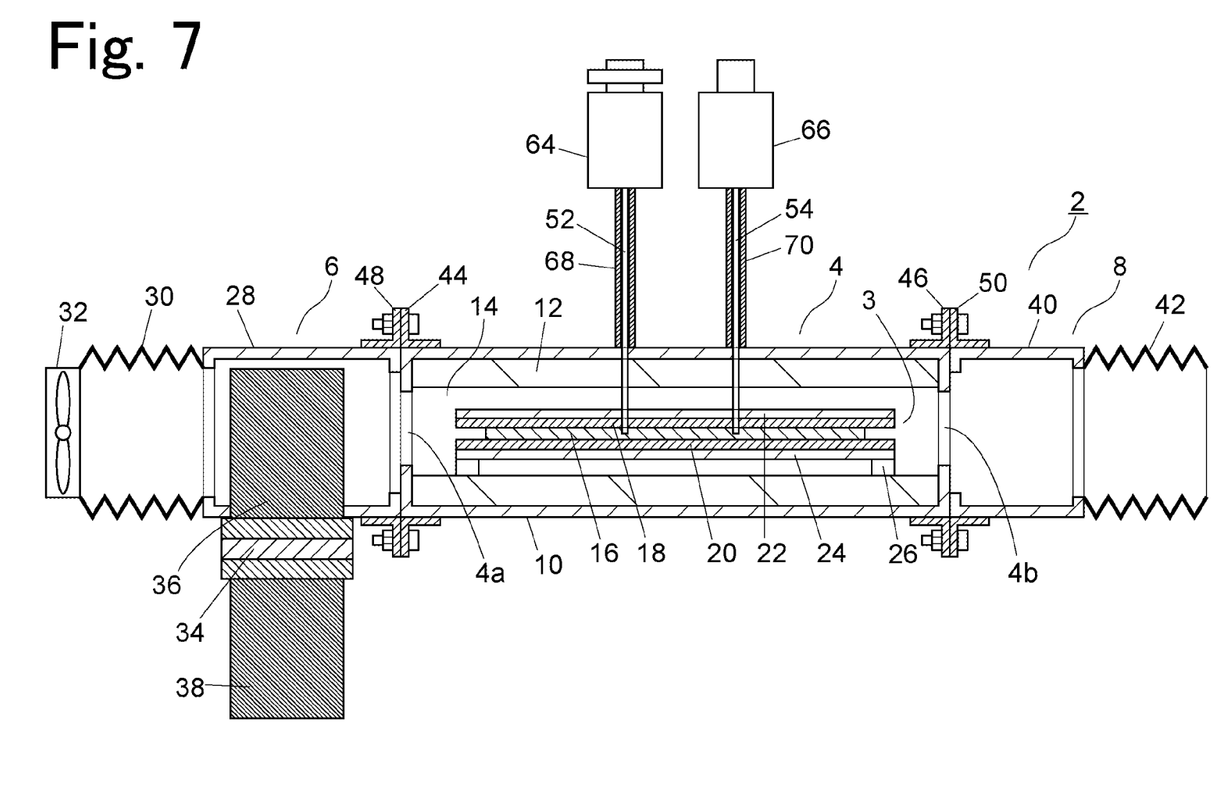
FIG. 7 is a cross-sectional diagram showing an example of a gas chromatography device.

An example of a gas chromatography device will be described with reference to FIG. 7. The gas chromatograph of FIG. 7 includes the column unit 2 described with reference to FIGS. 1 to 4, but the column unit 2a described with reference to FIGS. 5 and 6 may be alternatively provided.

The column unit 2 is arranged in such a way that the main plane of the column section 3 accommodated inside is horizontal, and prevents a temperature gradient from being generated by thermal convection with respect to the separation column 16. Both ends of the inner channel of the channel substrate forming the separation column 16 are communicated with the upper surface of the channel substrate, and are drawn out to the upper surface of the column section 3 through through holes provided to the heater 18 and the back plate 22. The transfer tubes 52 and 54 are connected respectively to the ends of the channel drawn out to the upper surface of the column section 3, and the ends are drawn out to the outside of the column cartridge 4 through holes provided to the insulating material 12 and the housing 10. Connection of the transfer tubes 52 and 54 to the column section 3 may be performed by adhesion by for example polyimide resin.

A sample injection section 64 is connected to the end of the transfer tube 52, and a detector 66 is connected to the end of the transfer tube 54. The parts of the transfer tube 52 and the transfer tube 54 which are exposed to the outside air are covered by transfer heaters 68 and 70, respectively, and are controlled to a constant temperature. As the transfer heaters 68 and 70, cylindrical ceramic heaters may be used, for example.

A sample introduced through the sample injection section 64 is introduced into the separation column 16 by a carrier gas through the transfer tube 52, and is separated into each component. A sample component separated by the separation column 16 is led to the detector 66 through the transfer tube 54, and is detected.

What is claimed is:

1. A column unit comprising:
   a tubular housing including a first opening and a second opening, and an inner space separated from outside air by an insulating material;
   an air cooling section arranged on a side of the first opening of the housing, the air cooling section including a cooling device;
   a fan arranged on a side of the first or second opening of the housing, the fan being controlled to operate, when cooling an inside of the inner space, to cause air to flow through the air cooling section in a direction from the side of the first opening to a side of the second opening, and not to operate when heating the inside of the inner space or maintaining the inside of the inner space at a constant temperature;
   a column section including a separation column, and. a heater for heating the separation column, the column section being arranged in the inner space of the housing in such a way that a gap through which air flows from the first opening to the second opening when the fan is operated is formed between the column section and an inner wall of the inner space;
   wherein the separation column is configured to include an inner channel, as a separation channel, on a flat channel substrate,
   the heater is a flat heater, and is arranged on at least one plane of the separation column,
   the column section has a stacked structure where the separation column and the heater are sandwiched between a pair of metal plates, and the heater is pressed against the separation column by the pair of metal plates, and
   the gap through which air is to flow is formed between the metal plates and the inner wall of the inner space.

2. The column unit according to claim 1, further comprising:
   a temperature sensor arranged in contact with the separation column or near the separation column; and a temperature control section for controlling operations of the beater and the air cooling section based on measured temperature of the temperature sensor.

3. The column unit according to claim 2, further comprising:
an air inlet door between the cooling device and the first opening of the housing, the air inlet door being for opening or closing the first opening,
wherein the temperature control section is configured to also control an operation of the air inlet door in such a way that the air inlet door closes at a time of heating of the separation column, and the air inlet door opens at a time of cooling of the separation column.

4. The column unit according to claim 3, further comprising:
an air outlet door for opening or closing the second opening of the housing,
wherein the temperature control section is configured to also control an operation of the air outlet door in such a way that the air outlet door closes, together with the air inlet door, at the time of heating of the separation column, and the air outlet door opens, together with the air inlet door, at the time of cooling of the separation column.

5. The column unit according to claim 2, wherein the temperature control section is configured to control the number of revolutions of the fan according to a capacity of the cooling device, or according to a type of a liquid phase of the separation column.

6. A gas chromatography device comprising:
a column unit comprising:
a tubular housing including a first opening and a second opening, and an inner space separated from outside air by an insulating material,
an air cooling section arranged on a side of the first opening of the housing, the air cooling section including a cooling device,
a fan arranged on a side of the first or second opening of the housing, the fan being controlled to operate, when cooling an inside of the inner space, to cause air to flow through the air cooling section in a direction from the side of the first opening to a side of the second opening, and not to operate when heating the inside of the inner space or maintaining the inside of the inner space at a constant temperature, and
a column section including a separation column, and a heater for heating the separation column, the column section being arranged in the inner space of the housing in such a way that a gap through which air flows from the first opening to the second opening when the fan is operated is formed between the column section and an inner wall of the inner space;
a sample injection section connected to an end of the separation column of the column unit;
a detector connected to another end of the separation column;
wherein the separation column is configured to include an inner channel, as a separation channel, on a flat channel substrate,
the heater is a flat heater, and is arranged on at least one plane of the separation column,
the column section has a stacked structure where the separation column and the heater are sandwiched between a pair of metal plates, and the heater is pressed against the separation column by the pair of metal plates, and
the gap through which air is to flow is formed between the metal plates and the inner wall of the inner space.

7. The gas chromatography device according to claim 6, further comprising:
a temperature sensor arranged in contact with the separation column or near the separation column; and
a temperature control section for controlling operations of the heater and the air cooling section based on measured temperature of the temperature sensor.

8. The gas chromatography device according to claim 7, further comprising:
an air inlet door between the cooling device and the first opening of the housing, the air inlet door being for opening or closing the first opening,
wherein the temperature control section is configured to also control an operation of the air inlet door in such a way that the air inlet door closes at a time of heating of the separation column, and the air inlet door opens at a time of cooling of the separation column.

9. The gas chromatography device according to claim 8, further comprising:
an air outlet door for opening or closing the second opening of the housing,
wherein the temperature control section is configured to also control an operation of the air outlet door in such a way that the air outlet door closes, together with the air inlet door, at the time of heating of the separation column, and the air outlet door opens, together with the air inlet door, at the time of cooling of the separation column.

10. The gas chromatography device according to claim 7, wherein the temperature control section is configured to control the number of revolutions of the fan according to a capacity of the cooling device, or according to a type of a liquid phase of the separation column.

* * * * *